US006915028B2

(12) United States Patent
Lyons

(10) Patent No.: US 6,915,028 B2
(45) Date of Patent: Jul. 5, 2005

(54) APPARATUS FOR AND METHODS OF SENSING EVANESCENT EVENTS IN A FLUID FIELD

(75) Inventor: Donald R. Lyons, Yorktown, VA (US)

(73) Assignee: Hampton University, Hampton, VA (US)

( * ) Notice: Subject to any disclaimer, the term of this patent is extended or adjusted under 35 U.S.C. 154(b) by 0 days.

(21) Appl. No.: 10/665,487

(22) Filed: Sep. 22, 2003

(65) Prior Publication Data

US 2004/0057647 A1 Mar. 25, 2004

Related U.S. Application Data

(63) Continuation of application No. 09/953,910, filed on Sep. 18, 2001, now Pat. No. 6,650,799.

(51) Int. Cl.[7] .................................................. G02B 6/00
(52) U.S. Cl. .............................. 385/12; 385/10; 385/37; 385/123
(58) Field of Search .............................. 385/12, 3, 5, 6, 385/10, 37, 39, 123

(56) References Cited

U.S. PATENT DOCUMENTS

| | | | | |
|---|---|---|---|---|
| 5,177,805 A | * | 1/1993 | Groger et al. | 385/12 |
| 6,137,442 A | * | 10/2000 | Roman et al. | 342/375 |
| 6,201,912 B1 | * | 3/2001 | Kempen et al. | 385/37 |
| 6,278,811 B1 | * | 8/2001 | Hay et al. | 385/13 |
| 6,361,299 B1 | * | 3/2002 | Quigley et al. | 428/36.3 |
| 6,550,342 B2 | * | 4/2003 | Croteau et al. | 73/800 |
| 6,597,821 B1 | * | 7/2003 | Bohnert et al. | 385/12 |

* cited by examiner

Primary Examiner—K. Cyrus Kianni
(74) Attorney, Agent, or Firm—Millen, White, Zelano & Branigan, P.C.

(57) ABSTRACT

An evanescent filed based sensor uses a detector for sensing variations in properties of a fluid flowing in a boundary layer adjacent to the detector. The detector comprises an optical waveguide in the form of an optical fiber having a core layer covered by a cladding layer and having a substantially D-shaped cross section defining a planar surface with an optical grating pattern thereon. When a beam of laser light is directed through the detector as an input, variations in an output of the beam of laser light are indicative of changes in fluid pressure or density in the boundary layer or immediate region adjacent to the grating of the optical waveguide.

8 Claims, 5 Drawing Sheets

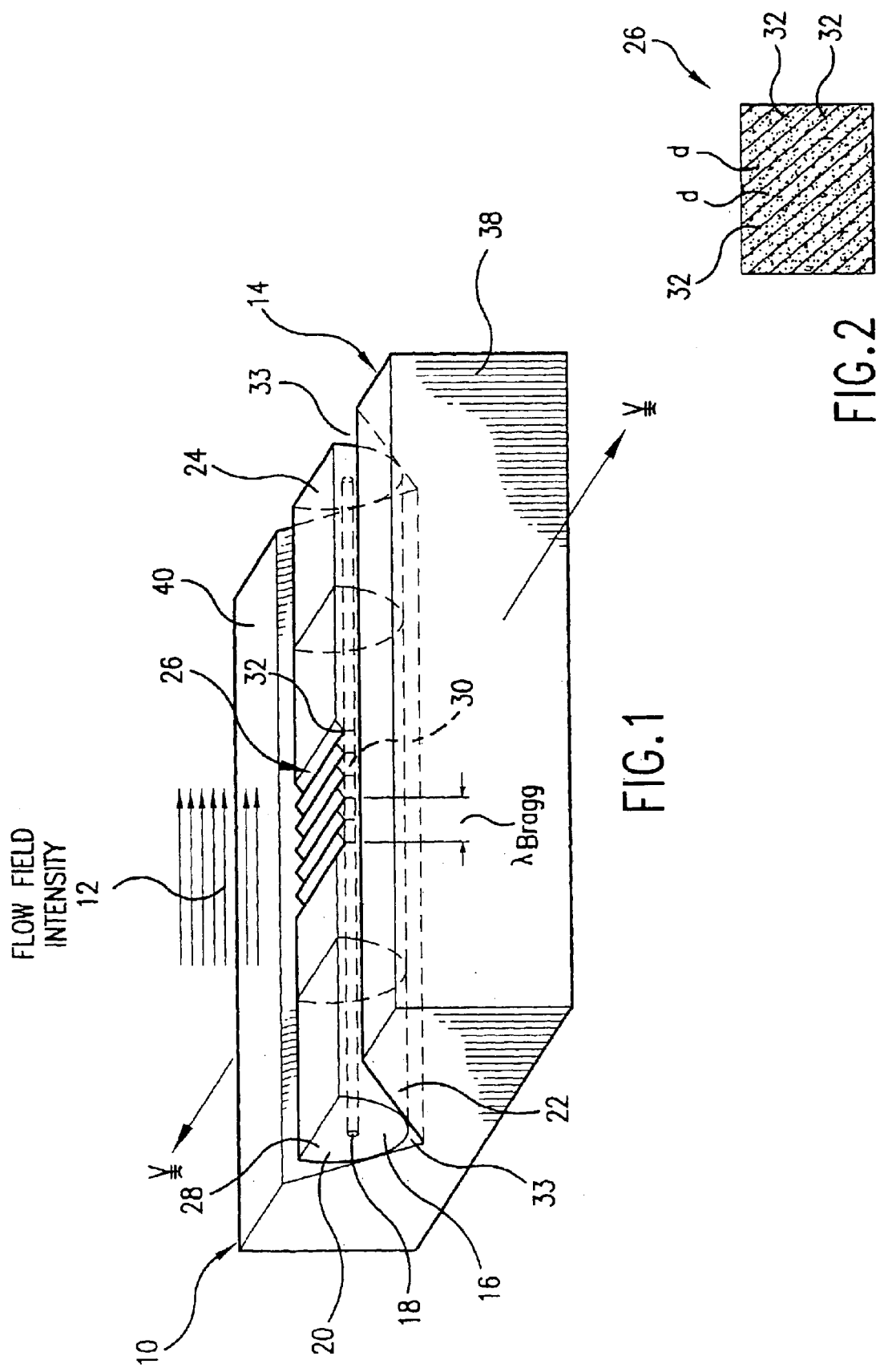

APPARATUS FOR AND METHODS OF SENSING EVANESCENT EVENTS IN A FLUID FIELD

This application is continuation of application No. 09/953,910 filed on Sep. 18, 2001.

FIELD OF THE INVENTION

The present invention is directed to an apparatus for and methods of sensing evanescent events in a fluid field. More particularly, the present invention is directed to such apparatus and methods using an evanescent field based fluid sensor which utilizes non-intrusive fiber optic technology to sense hydrodynamic conditions.

BACKGROUND OF THE INVENTION

There is a need for sensors which detect hydrodynamic flow conditions, as well as fluid density conditions and variations, in a manner that reflect true conditions in that the sensor structure itself does not interfere with fluid flow at the location being monitored. For example, in monitoring fluid flow conditions over an airfoil, it is advantageous from both testing and fluid control purposes to know how the fluid environment is interacting with the airfoil at a specific, but perhaps fleeting moment. This is because slight variations in fluid dynamic conditions can over even very short periods of time give rise to situations of considerable interest. This is not only an issue in aerodynamics, but is also of great interest in medical applications where the flow of blood through the circulatory system is monitored. This is because circulating blood is constantly changing in pressure, velocity and density as a myriad of physiological conditions react with the blood stream.

The ability to detect fleeting changes in fluid flow conditions is useful in many other situations, such as but not limited to, the flow of fluids in hypersensitive chemical processing plants and the flow of gases through systems such as air conditioning ducts and gas scrubbing systems. There are many situations in which maintenance of laminar fluid flow is important, such as air induction systems of internal combustion engines, wherein laminar flow of combustion air is important to maximize efficiency in order to reduce pollutants and fuel consumption.

The need for non-intrusive, i.e., small, fluid sensors is also apparent in the marine industry in which vehicles are propelled through two fluids simultaneously, i.e., air and water, which fluids are separated by a very complex interface. Maximizing the efficiencies of hydrodynamic surfaces on marine vessels requires knowledge of what occurs or is occurring at boundary layers directly adjacent to or perhaps even perhaps within skin structure defining the surfaces.

Further examples of the need to understand and thereby control fluid flow over surfaces are exemplified by the need of next-generation lighter-than-air cargo and passenger air ships and by competition to improve the effectiveness of sails on racing boats such as America's Cup yachts.

Currently, the complexities encountered when attempting to comprehend boundary layer flow are perhaps best understood through three scalar partial differential equations that describe conservation of momentum for motion of a viscous, incompressible fluid. These complexities are frequently expressed mathematically in one complex expression, which relates fluid density, fluid velocity, fluid pressure, body force, and fluid viscosity. This equation has few mathematical solutions. Thus, a sensor which effectively monitors boundary layer conditions would be of considerable assistance in coping with, and effectively functioning within, an area of technology that has historically been extremely difficult to comprehend due to its complexity.

SUMMARY OF THE INVENTION

In view of the aforementioned considerations, a detector for sensing variations in properties of a fluid flowing in a boundary layer adjacent to the detector comprises an optical waveguide having a core covered by a cladding. The optical waveguide has a planar surface with an optical grating pattern thereon. When a laser beam is directed through the detector, a probing beam is modulated by the grating in a way which is indicative of changes in fluid properties in the boundary layer adjacent to the grating.

In accordance with a more specific aspect of the invention, the optical waveguide is an optical fiber with a D-shaped cross-section; the optical fiber having the core disposed adjacent to the planar surface with the grating formed in the cladding adjacent to the core.

In accordance with a further aspect of the invention the grating has a first portion and a second portion, and in still a further aspect of the invention, the second portion is spaced from the first portion by a selected distance.

The invention may also be expressed as directed to a system for sensing variations in flow field intensity of a fluid flowing in a boundary layer adjacent to a body exposed to the fluid. The system comprises an optical fiber on or in the body, the optical fiber having a core covered by cladding and a D-shaped cross-section. The D-shaped cross-section defines a planar surface adjacent the core. The planar surface has an optical grating thereon. A tunable laser produces a laser beam which is directed through the optical fiber. Before passing through the optical fiber, the laser beam is directed through a beam splitter which produces a fiber probing beam and a reference beam. The fiber probing beam passes through the optical fiber and interacts with the optical grating while the reference beam is directed to a first sensor so as to produce a reference output indicative of the amplitude of the reference beam. A second sensor detects the fiber probe beam after it has been modulated by the grating and produces a modulated output indicative of the amplitude of the probe beam as modulated by the grating. A comparator is connected to the first and second sensors for receiving the reference output and the modulated output so as to produce a differential signal indicative of the flow field intensity in the boundary layer adjacent to the body.

In further aspects of the invention, the tunable laser is a narrow linewidth, tunable laser which is passed through an optical chopper disposed between the laser and the beam splitter. In still further aspects of the invention, the first and second sensors are photodiodes and the optical grating comprises at least first and second grating portions.

The invention is also directed to methods for sensing variations in properties of a fluid flowing in a boundary layer adjacent to a detector, wherein the method comprises directing a beam of laser light through an optical waveguide. The optical waveguide has a core layer covered by a cladding layer defining a planar surface with an optical grating pattern thereon. Variations in an output of the beam of laser light are detected, which variations are indicative of changes in fluid pressure or on density in the boundary layer adjacent to the grating of the optical waveguide.

The method further comprises configuring the optical waveguide as an optical fiber with a D-shaped cross-section.

In a more specific aspect of the method, the optical fiber has an optical grating with first and second portions having line spacings corresponding to first and second Bragg angles, respectively. The laser beam is forward coupled by the first portion and forward and reversed coupled by the second portion to sense fluid conditions in the boundary layer so as to modulate the laser beam output and to also provide a reference beam.

BRIEF DESCRIPTION OF THE DRAWINGS

Various features and attendant advantages of the present invention will be more fully appreciated as the same becomes better understood when considered in conjunction with the accompanying drawings, in which like reference characters designate the same or similar parts throughout the several views, and wherein:

FIG. 1 is a perspective view showing a detector configured in accordance with the principles of the present invention for sensing variations in properties of a fluid;

FIG. 2 is a planar view of a corrugated optical grating;

DETAILED DESCRIPTION OF THE DRAWINGS

Figure 3:
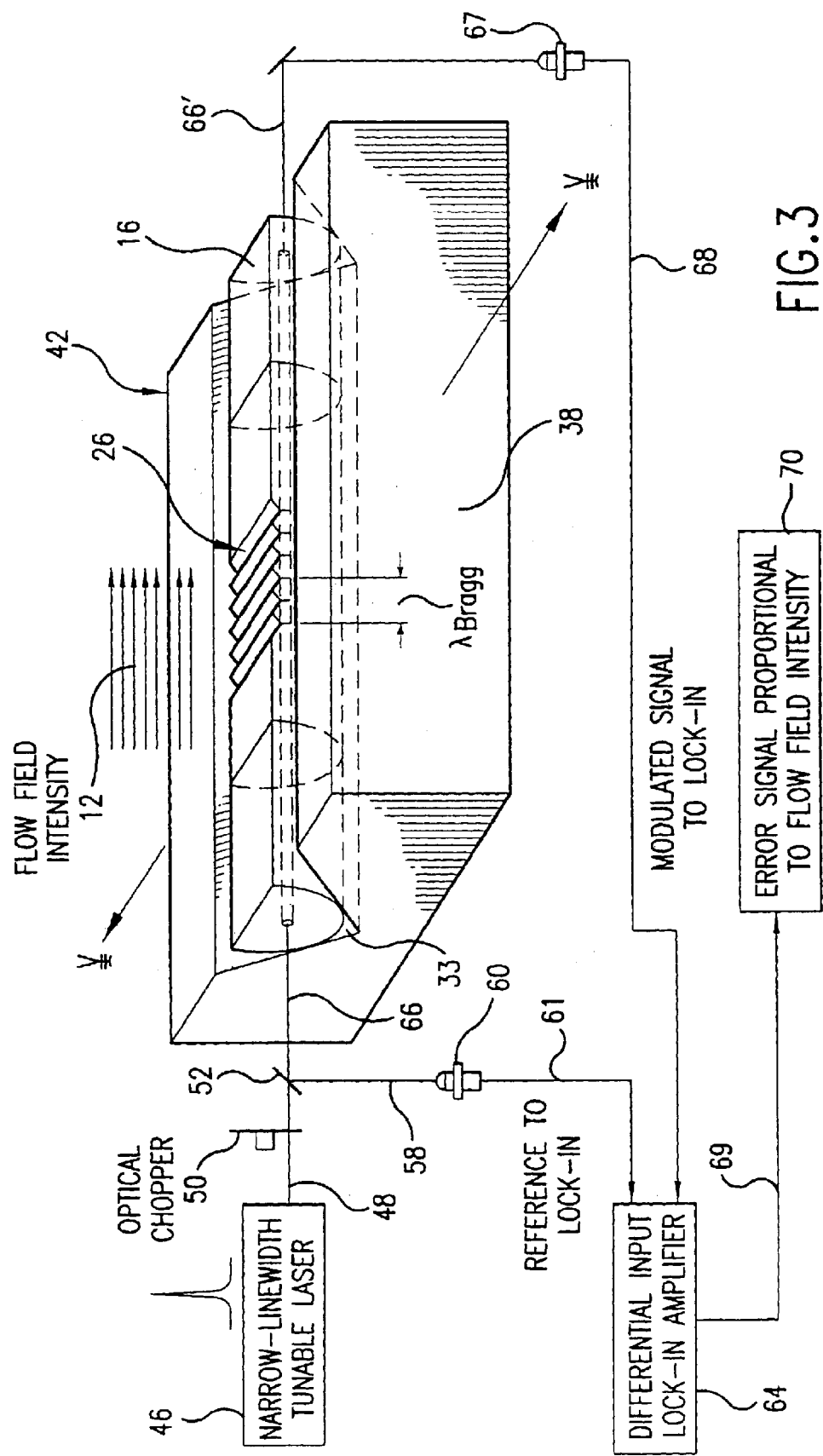
FIG. 3 is a diagrammatic illustration of a system for sensing variations in flow field intensity of a fluid utilizing the detector of FIG. 1.

Referring now to FIG. 1, there is shown optical detector arrangement 10, configured in accordance with the principles of the present invention, for sensing variations in intensity of a fluid flow field 12 disposed adjacent to a body 14. In the illustrated embodiment, the optical detector arrangement 10 preferably utilizes an optical fiber 16 comprised of a core 18 surrounded by cladding 20. While an optical fiber 16 is preferred as a detector, other configurations could be used, for example, wafers which could be rectangular, round or have any shape which would perform according to the principles of the present invention.

As seen in FIG. 1, the optical fiber 16 has a D-shaped cross-sectional profile with a semi-cylindrical or elliptical surface 22 and a planar surface 24. Planar surface 24 is disposed adjacent to the fluid flow field 12 and has an optical grating 26 in a portion 28 of the cladding 20 that overlies the core 18 in a region 30 of the core. The grating 26 has lines 32 spaced a selected distance apart which result in Bragg angle reflections or resonant mode coupling for a selected Bragg wavelength $\lambda_{Bragg}$. In the example of FIG. 1, the grating 26 is a corrugation formed by ablation of the cladding 20, however the grating may also be formed optically by photo-induced index changes.

The D-shaped optical fiber 16 is preferably mounted in a V-shaped groove 33 in a body 38 with a locally planar surface 40, the D-shaped optical fiber 16 having only its planar surface 24 exposed to the flow field 12 so that the planar surface 40 of the body 38 is coincident, if not parallel with the planar surface 24 of the optical fiber. As is set forth earlier in this application, the body 38 can be any body over which the fluid 12 flows, such as but not limited to an air foil, a surface of a ship, a submarine, a medical instrument, a sail, or any other instrumentality. Since the fiber 16 is flush with the surface 40 of the body 14, the resulting sensor is non-intrusive and can measure properties of hydrodynamic flow, fluid density and phase change by detecting minute variations in actual boundary layer conditions. Thus, through evanescent coupling, fleeting changes in intensity of the flow field 12 are detectable.

The sensor of FIG. 1 is designed such that in the stationary condition, i.e. no fluid flow, nearly 100% of the guided mode, i.e. passage of light through the core 18, is coupled out of the optical fiber 16 in the vicinity of the grating 26. The responses of the sensing arrangement 10 to pressure changes under both subsonic and hypersonic flow conditions are related to induced periodic boundary conditions imposed on the D-fiber structure by fabrication of the grating. These same responses are governed by Bernoulli conditions within the boundary layer adjacent to the optical fiber 16. Since the relationship between pressure and fluid density within the boundary layer affects the evanescent filed coupling between the guided and unguided modes of the optical fiber 16 i.e. the core 18 and cladding 20, respectively, small deviations from a resulting output null are directly related to pressure differentials.

Referring now to FIG. 3, the detector arrangement 10 of FIG. 1, comprising the optical fiber 16 and the body 38, is utilized in combination with a system 42 for detecting variations in a fluid flow field 12. In the system 42 of FIG. 3, a narrow linewidth, tunable laser 46 having automated, wavelength scanning capabilities is employed to direct a laser beam 48 through an optical chopper 50 and beam splitter 52. The laser 46 is a single frequency laser, tuned to the Bragg resonance of the optical fiber 16 set by the Bragg wavelength $\lambda_{Bragg}$ in order to generate a null during stationary state conditions in which there is no flow field 12 i.e. when the velocity of the fluid flow field is zero. Ideally, when in the null condition, there is no light exiting the fiber because there is complete evanescent field coupling of the guided light in the core 18 with the unguided light in the cladding 20 due to subsequent coupling outside of the fiber. The null condition occurs in the immediate region 30 of the periodic patterns formed by the grating 26 before the light reaches the exit end of the optical fiber.

In accordance with the present invention, the beam splitter 52 provides a reference beam 58 which is sensed by a first photodiode 60. The output 61 of the first photodiode 60 is transmitted to a differential input, lock-in amplifier 64. The beam splitter 52 also provides a probing beam 66 which passes through the optical fiber 16 and interacts with the grating 26 in the cladding 20 while being guided through the core 18. Thus a modulated probing beam 66' is detected by a second diode 67 which has an output 68 proportional to the amplitude of the modulated probing beam 66'. The output 68 of the second diode 67 is transmitted to the differential input, lock-in amplifier 64 where its amplitude is compared to that of the output 61 from the diode 60 which senses the reference beam 58. The lock-in amplifier 64 has an output signal 69 which is transmitted to a monitoring circuit 70. The monitoring circuit 70 may provide any number of functions which relate to the body 38, such as but not limited to controlling the body 38 or some related element with respect to the field flow, displaying variations in flow field intensity or storing detected conditions for later review and use.

When the outputs 61 and 68 of the first and second photodiodes 60 and 67 cannot be made to match, the output 69 to the monitoring circuit 70 is not a null. Rather, the output 69 is a signal having an intensity proportional to the difference in amplitude between the output 68 of the second photodiode 67 which detects the modulated signal 66' and the amplitude of the reference signal 61 from the first photodiode 60. Since pressure or density are direct functions of changes in flow field intensity 12, the monitor 70 can utilize Bernoulli's law to determine the speed of the flow field 12 over the body 38. The arrangement can also be used to sense a change in state. For example, if the fluid flow field changes from air and water vapor to ice on an airfoil surface 40, the boundary layer is no longer adjacent the airfoil surface. In its stead is a substance (ice) of a markedly different index of refraction so that the detection system 10 generates an immediate output notifying an aircraft pilot that ice has formed on an airfoil. Another example of a change in state occurs in liquids where there can be an abrupt change in pressure due to formations of cavities within liquids adjacent a solid surface.

The material composition of the optical fiber 16 of FIGS. 1–3 is high grade fused silica over-cladding 20 with a fluorine-based silica cladding and a Ge and F-doped core region 18 beneath (roughly 10 μm for 820 nm D-fiber) the flat portion of the fiber 16. Due to the general nature of glass, the dimensions of D-fibers can be easily varied during their manufacture. However, due to typical wavelengths requirements associated with Ge-doped optical waveguides, the optical fiber 16 is generally made in a variety of five commercial dimensions corresponding to five key fiber and/or laser source wavelengths. These wavelengths, technically known as cutoff wavelength are 550±60 nm (allowing the single mode operation of the He—Ne 633 nm gas and the 670 nm semiconductor lasers), 700±60 nm (corresponding to semiconductor lasers at 820 nm), 890±70 nm (corresponding to semiconductor and fiber lasers at 890, 980, and 1060 nm), 1040±70 nm (corresponding to 1300 nm semiconductor lasers and the first low loss transmission window of telecommunication-grade Ge-doped optical fibers), and 1290±70 nm cutoff (corresponding to the 1500–1550 nm range semiconductor lasers and the lowest loss transmission window for Ge-doped optical waveguides). The cutoff wavelength is the wavelength below which single mode operation is no longer possible. Therefore, the single mode operating bands corresponding to the cutoff wavelengths given above are: 610–700, 760–900, 960–1250, 1110–1400, and 1360–1680 nm, respectively. The fiber diameters corresponding to these five cutoff wavelengths are 70, 80, 125, 125, and 125 μm, respectively.

Exemplary of a non-intrusive configuration for the hydrodynamic detector 10 using a D-fiber for 1550 nm operation is a D-fiber having a cross-sectional diameter of 125 μm (O.D.) and a flat width of 121 μm. The core 18 is located 16 μm from the planar surface 24 of the optical fiber 16. Since optical fibers 16 of various dimensions are made from similar fiber preforms with high dimensional tolerances, all measurements scale proportionately for the various fiber diameters.

Considering now the corrugation spacing of gratings, it is evident from the nature of electromagnetic mode coupling that the wavelength parameters are strongly dependent upon pattern depth, since the evanescent field associated with the single guided mode in question diminishes quite rapidly and requires proximity interaction with these corrugated patterns or gratings 26. This is so because in all practical implementations of this device it is desirable to couple (or null) the guided modes over as short a distance as possible. The following are two examples of parameter sets associated with coupling 100% of the light out of the fiber core 18 at steady state.

| Example 1: | Example 2: |
|---|---|
| Nominal Mixing half-Length 675.858 μm | Nominal Mixing Half-Length 292.625 μm |
| Corrugation depth 0.2 μm | Corrugation depth 0.5 μm |
| Spacing 19.5791 μm | Spacing 19.5791 μm |
| Nominal sensed index 1.37 | Nominal sensed index 1.37 |
| Nominal Laser Wavelength 1.52 μm | Nominal Laser Wavelength 1.52 μm |

Since the resonance is very sharp, it is important for a practical device to use a tunable laser source such as a tunable semiconductor unit operating in the 1500 to 1550 nm wavelength range. This principle translates to any tunable or nontunable systems capable of allowing the joint conditions of being on resonance and initiating a guided fiber mode that is resonant with an unguided mode through the interaction of its evanescent field with these corrugations (in the case of the etched or ablated patterns in question).

Figure 4:
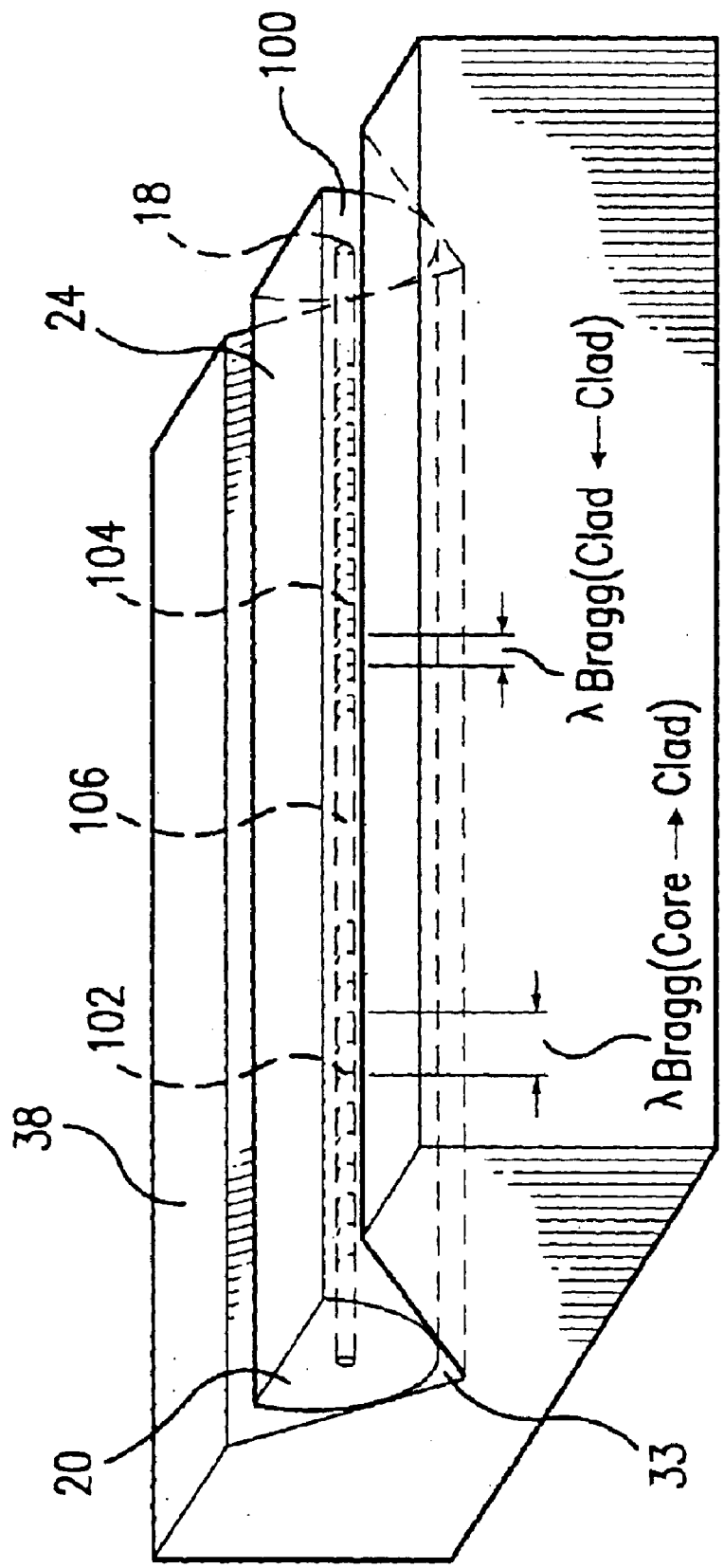
FIG. 4 is a perspective view of a second embodiment of a detector configured in accordance with the principles of the present invention.
Figure 5:
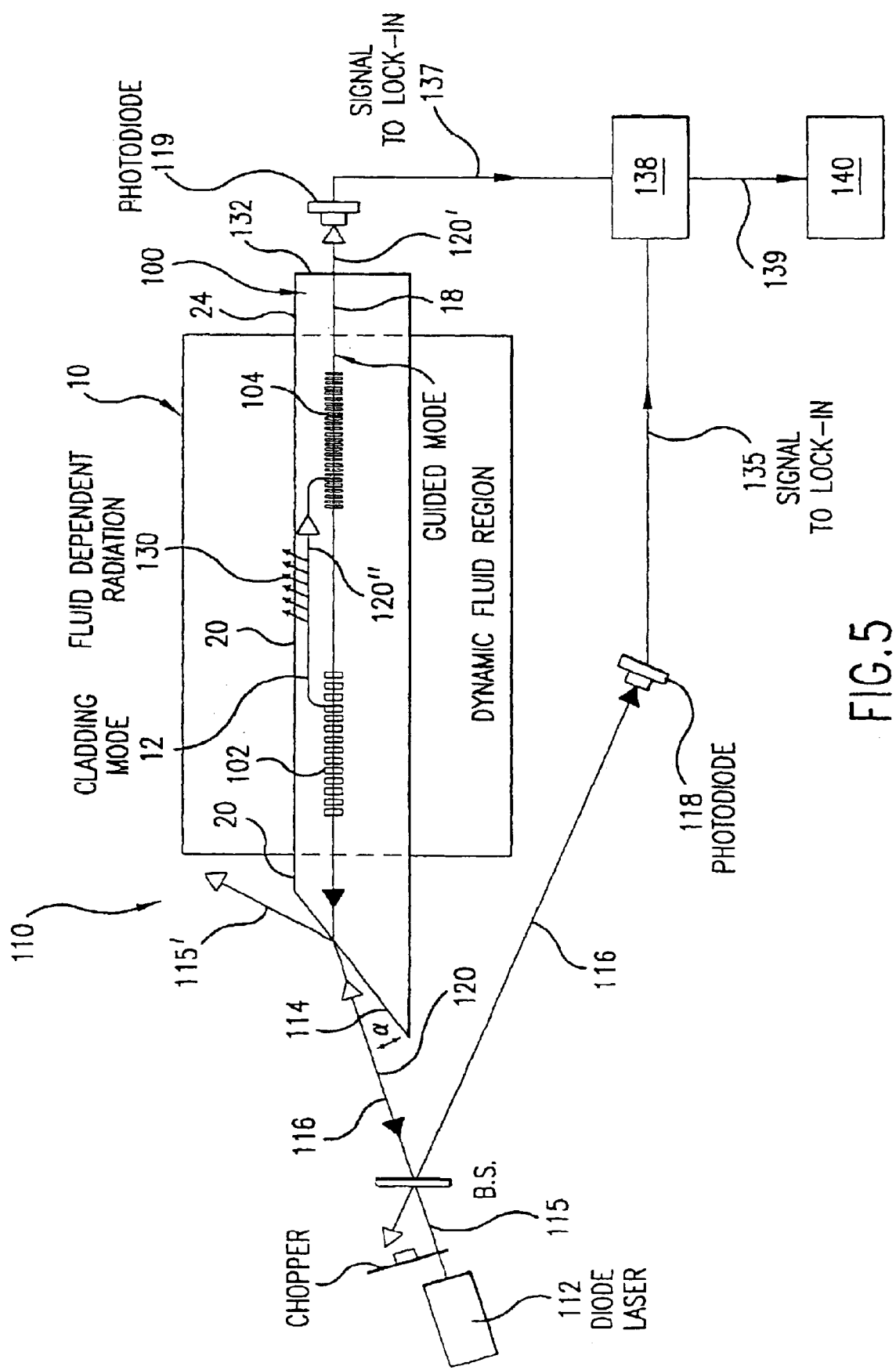
FIG. 5 is a schematic view of a system for sensing variations in flow field intensity or dynamic index variations of a fluid utilizing the detector of FIG. 4.

Referring now to FIGS. 4 and 5 there is shown, optical fiber 100 configured in accordance with the principles of the present invention. The optical fiber 100 is D-shaped in a manner similar to the optical fiber 16 of FIGS. 1–3 and is preferably mounted on (or rather in) a body 38 with only its planar surface 24 exposed. Instead of having single optical grating 26 as in FIGS. 1–3, the optical fiber 100 of FIGS. 4 and 5 has a pair of optical grating portions 102 and 104. The grating portions 102 and 104 are shown separate by a gap 106. As with the optical fiber 16, the optical fiber 100 has core 18 and cladding 20. Preferably, the periodic variations forming the gratings 102 and 104 are produced by photo-induced index of refraction modulations and thus are less fragile and more ameanable to multi-pattern interactions and sensor design modifications.

The first grating portion 102 has spacing defined by the wavelength $\lambda_{Bragg\ (Core \to Clad)}$ while the second grating portion 104 has spacing defined by the wavelength $\lambda_{Bragg\ (Clad \leftarrow Clad)}$. This dual pass arrangement effectively doubles the interaction length in the gap 106 and thus heightens the sensitivity of the detector.

The optical fiber of 100 of FIG. 4 is used in combination with a system 110 of FIG. 5 for detecting variations in the fluid flow field 12 by utilizing back reflections within the optical fiber 100. As is seen in FIG. 5, a diode laser 112 is disposed at an angle a with respect to the input face 114 of the optical fiber 100 in order to eliminate spurious signals 115' that could originate from the fiber input end. In the embodiment of FIG. 5, the input base 114 is disposed obliquely with respect to the axis of optical fiber 100. This allows the grating induced back-reflection phenomena of laser beam 115 illustrated by the black arrows 116, with portions of forward coupling, illustrated by white arrows 117, to be void all modulating effects except the actual signals of interest. The following relationship results for Bragg pattern spacing in the case of back reflection in a guiding medium:

$$\Lambda_B = \frac{\pi}{\beta} \Rightarrow \Lambda_{B_c} = \frac{\pi}{\beta_c} \text{ and } \Lambda_{B_{cl}} = \frac{\pi}{\beta_{cl}}$$

where c and cl are the fiber core 18 and cladding 20 indices, respectively. Similarly, for core-clad forward coupling, the following relationship holds:

$$\Lambda_{B_{c \to cl}} = \frac{2\pi}{\beta_c - \beta_{cl}} \text{ or } \frac{1}{\Lambda_{B_{c \to cl}}} = \frac{1}{2\Lambda_{B_c}} - \frac{1}{2\Lambda_{B_{cl}}} = \frac{\beta_c}{2\pi} - \frac{\beta_{cl}}{2\pi}, \therefore$$

$$\frac{2}{\Lambda_{B_{c \to cl}}} = \frac{1}{\Lambda_{B_c}} - \frac{1}{\Lambda_{B_{cl}}}.$$

Note that $\Lambda$ is approximately equal n $k_{vac}/\pi$ so that the last expression can be rewritten as $$\Lambda_{B_{c \to cl}} \geq 2\pi / (n_c - 2n_{Sensed})$$

As is seen in FIG. 5, sensing signal system 110 functions somewhat similar to the system of FIG. 3 with a first photodiode 118 providing the dominant modulated signal output proportional to the amplitude of the grating induced back reflected probe beam 116 and a second photodiode 119 providing a conjugate output proportional to the amplitude of the forward coupled portion of the modulated probe beam 120' which has been and passed through the optical fiber 100. In FIG. 5, a forward coupled beam 120 is transmitted through the cladding layer 20 so as to emit fluid dependent radiation 130 which is affected by boundary conditions 12 adjacent the planar surface 24 of the optical fiber 100, while the back reflected beam 120" in the cladding 20 emits similar fluid dependent radiation as it retraces the path of beam 120 and is not transmitted out of the end 132 of optical fiber 100. Due to coupling of the beam 120' transmitted though the cladding 20 and the second grating 104, the beam 120' is minimally forward coupled out of the optical fiber 100 and is detected and measured by the photodiode 119, its amplitude having been diminished substantially by fluid conditions in the boundary layer 12 adjacent to the cladding 20.

Similar in setup but somewhat different from the arrangement of FIG. 3, the first photodiode 118 and the second photodiode 119 have outputs 135 and 137. These could be respectively connected to the input and/or normalization channels of a lock-in amplifier 138. This would allow the detection of amplitude modulations of the outputs 135 and 137 to produce a signal 139 that is proportional to the dynamic variations in fluid density or fluid pressure in the boundary layer or the fluid region adjacent to the optical fiber 100. The signal 139 is then transmitted to a monitoring circuit 140 which functions similar to the monitoring circuit 70 of FIG. 3.

The following derivations pertain to coupled mode grating formulations for the optical waveguide sensor 100 of FIGS. 4 and 5.

Starting with the wave equation for a perturbed dielectric medium we have, $$\nabla^2 E = \frac{1}{c^2}[\varepsilon + \delta\varepsilon]\frac{\partial^2 E}{\partial t^2} \text{ and}$$

$$E = E(r, z, t) = \text{Re}\left\{\sum_m [A_m^{(+)}(z)e^{i\beta_m z} + A_m^{(-)}(z)e^{-i\beta_m z}]\xi_m(r)e^{-i\omega t}\right\}$$

where r is the transverse coordinate, m the mode number, $A^{(+)}$ and $A^{(-)}$ are the respective forward and reverse moving field amplitudes, $\xi_m$ are the unperturbed mode eigenfunctions, and $$\delta\varepsilon(\bar{r},z) = \delta n^2(r)\cos(2\pi z/\Lambda) \text{ is the "pattern written in the fiber"}.$$

For reflections of the $m^{th}$ mode, $$\frac{dA_m^{(\pm)}}{dz} = \pm i\kappa_m e^{-2i(\beta_m - \pi/\Lambda)z}A_m^{(\mp)}$$

is our "coupled differential equation" with the coupling parameter given by $$\kappa_m = \left(\frac{\omega}{c}\right)^2 \int \delta n^2(r)|\xi_m(\bar{r})|^2 d^2r / 2\beta \int |\xi_m(\bar{r})|^2 d^2r.$$

Recalling that the condition for resonance reflection is given by $\Delta = \pi/\beta_m$ and $A_m^{(-)}(z=L)=0$ where L is the pattern length.

Thus the forward and reverse mode amplitudes are given by the following expressions:

$A_m^{(+)}(z) = A_m^{(+)}(0)[\cos h(\kappa_m z) + \tan h(\kappa_m L)\sin h(\kappa_m z)]$ and
$A_m^{(-)}(z) = A_m^{(+)}(0)[\sin h(\kappa_m z) + \tan h(\kappa_m L)\cos h(\kappa_m z)].$ The forward propagating modes obey the following equations:

$$\frac{dA_m^{(+)}(z)}{dz} \approx$$

$$i\left[\sum_s \kappa_{ms} e^{i(\beta_s - \beta_m + 2\pi/\Lambda)z} A_s^{(+)}(z) + \int K_m(q) e^{i(q_s - \beta_m + 2\pi/\Lambda)z} A_q(z) dq\right]$$

where $$\kappa_{ms} = \left(\frac{\omega}{c}\right)^2 \int \delta n^2(r)\xi_m(\bar{r})\xi_s(\bar{r})d^2r \bigg/ \left(4\beta_m\beta_s \int |\xi_m(\bar{r})|^2 d^2r \int |\xi_s(\bar{r})|^2 d^2r\right)^{\frac{1}{2}}$$

where the first term on the right hand side of the equation represents discrete modes and the second term denotes continuum or radiation modes. There are similar expressions for mode mixing between two continuum modes. Finally, for resonant mode mixing between the guided mode with propagation constant $\beta_o$ and an arbitrary radiation mode with propagation constant $\beta_r$ where $\beta_o - \beta_r = 2\pi/\Lambda$, the following expressions can be written assuming no radiation losses and initial condition $A_r^{(+)}(0) = 0$:

$$A_o^{(+)}(z) = A_o^{(+)}(0)\cos\left[\frac{1}{2}\left(\frac{\omega}{c}\right)^2 \frac{\kappa_{or}z}{\sqrt{\beta_o\beta_r}}\right]$$

$$A_r^{(+)}(z) = i\sqrt{\frac{\beta_o}{\beta_r}} A_o^{(+)}(0)\sin\left[\frac{1}{2}\left(\frac{\omega}{c}\right)^2 \frac{\kappa_{or}z}{\sqrt{\beta_o\beta_r}}\right].$$

The forward and reverse moving field amplitudes $A_o$ and $A_r$ correspond to the amplitudes of the modulated probe beam 120 and back reflected beam 116 of FIG. 5 which produce voltage outputs 135 and 137 which are compared in the differential input, lock-in amplifier 138.

Figure 6:
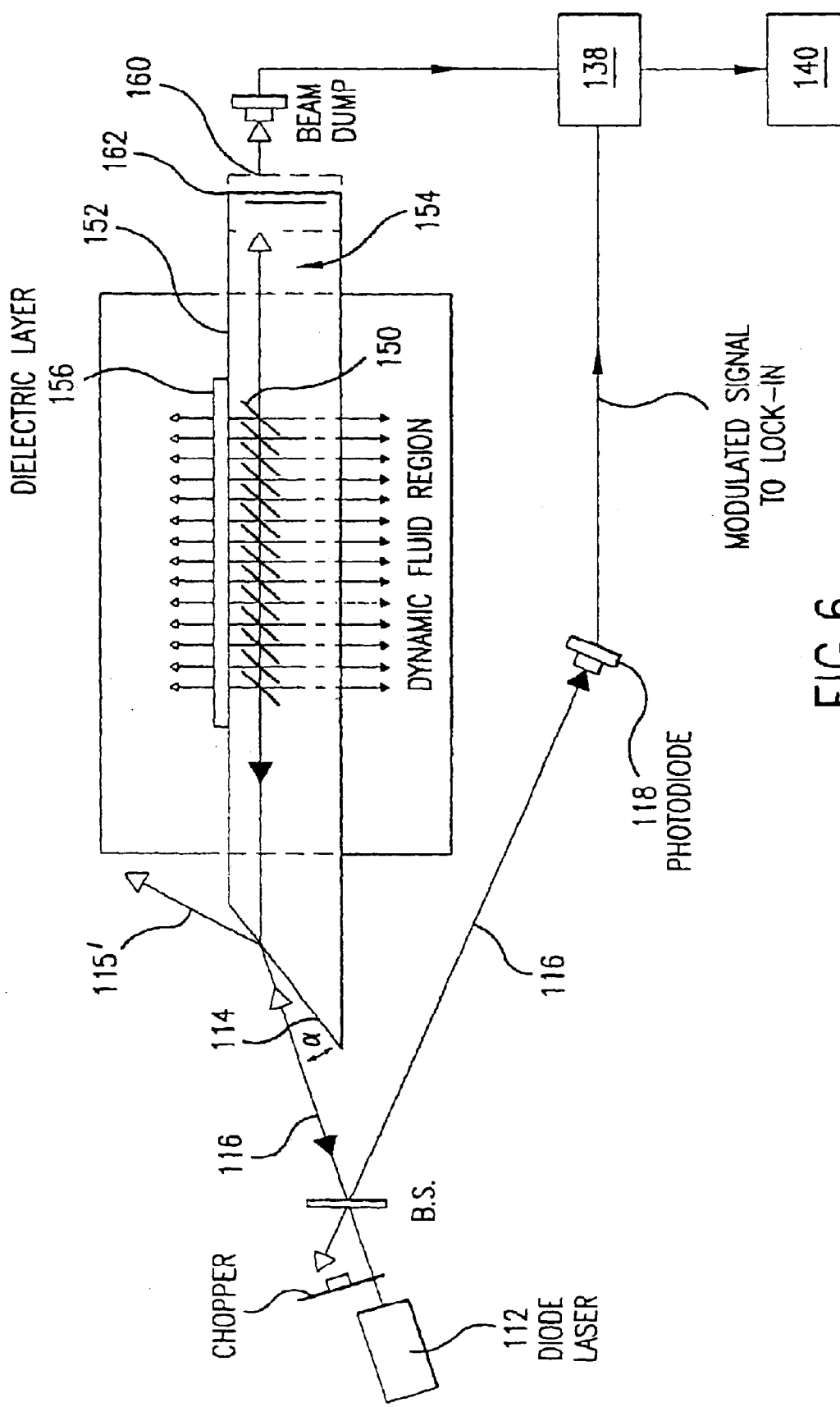
FIG. 6 is a schematic view similar to FIG. 5 but showing a third embodiment of a detector in accordance with the principles of the present invention.

In FIG. 6 an optical grating 150 is slanted with respect to the planar surface 152 of the optical fiber 154, for example, preferably at an angle of 45°. In this embodiment an anti-reflective coating or dielectric layer 156 made of a material such as, for example, magnesium fluoride ($MgF_2$), is disposed over the cladding 158. The dielectric layer 156 has a thickness of one half the wavelength of the beam to increase reflection back into the optical fiber 154. A beam dump 160 to minimize beam reflection is disposed at the end 162 of the optical fiber 154. This arrangement is suitable for situations in which the optical fiber index n substantially equals 1.414.

This invention describes fiber optic sensing devices, based upon evanescent field coupling in a D-shaped fiber with periodic patterns. In particular, these patterns are either created by physical ablation (resulting in the removal of material) or by photo-induced index changes. In either case, the objective is the coupling of light out of the guided region or core 18 of a fiber 16 or 100 and into the unguided regions or cladding 20 in order to null the light throughput resulting from normal guidance. This leads to a situation in which external changes in the outer vicinity of the fiber strongly influence the null state and give rise to straightforward extraction of information concerning dynamic states in regions immediately external to the optical fiber 10 or 100 such as the boundary layer 12. Since the change in the null condition is directly related to locally external environment (i.e., only in locations where the periodic patterns exist), this information can be transmitted to a remote observer at either end of the optical fiber 10 or 100.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A detector for sensing variations in properties of a fluid flowing in a boundary layer adjacent to the detector, the detector comprising an optical waveguide having a core layer covered by a cladding layer defining a planar surface with an optical grating pattern thereon, the optical grating pattern being exposed to the flowing fluid wherein when a beam of laser light is directed through the detector as an input while the fluid is flowing over the optical grating, variations in an output of the beam of laser light are indicative changes in fluid pressure or density in the boundary layer adjacent to the grating of the optical waveguide.

2. A detector according to claim 1 wherein the optical waveguide is an optical fiber with a D-shaped cross section defining a planar surface and wherein the core is adjacent to the planar surface and the grating is formed in the cladding.

3. A detector according to claim 2 wherein the grating has a first portion and a second portion, the second portion being spaced from the first portion by a selected distance.

4. A detector according to claim 2 wherein the optical grating pattern is slanted at an angle with respect to the planar surface of the fiber.

5. A detector according to claim 4 wherein the angle is 45°.

6. A method for sensing variations in properties of a fluid flowing in a boundary layer adjacent to a detector, the method comprising:

directing a beam of laser light through an optical waveguide having a core layer covered by a cladding layer and defining a planar surface with an optical grating pattern thereon, and detecting variations in an output of the beam of laser light indicative changes in fluid pressure or density in the boundary layer adjacent to the grating of the optical waveguide while the fluid is flowing over the grating pattern.

7. A method according to claim 6 wherein the optical waveguide is an optical fiber with a D-shaped cross section and wherein the core is adjacent to the planar surface and the grating pattern is formed in the cladding.

8. A method according to claim 7 wherein the grating pattern has a first portion and a second portion, the second portion being spaced from the first portion by a selected distance.

* * * * *